United States Patent [19]

Kopp

[11] Patent Number: 5,112,622

[45] Date of Patent: May 12, 1992

[54] INTRAVENOUS SOLUTIONS FOR INFLUENCING RENAL FUNCTION AND FOR MAINTENANCE THERAPY

[76] Inventor: Klaus F. Kopp, Asslkofener Strasse 4, D-8017 Ebersberg, Fed. Rep. of Germany

[21] Appl. No.: 467,166

[22] Filed: Jan. 19, 1990

[51] Int. Cl.⁵ .................. A01N 59/08; A01N 59/10; A61K 33/14
[52] U.S. Cl. .................................. 424/663; 424/665; 424/678; 424/679; 424/680; 424/715; 424/717
[58] Field of Search ............... 424/663, 665, 678, 679, 424/680, 715, 717

[56] References Cited

U.S. PATENT DOCUMENTS

| | | | |
|---|---|---|---|
| 4,289,750 | 9/1981 | Kopp et al. | 424/81 |
| 4,548,817 | 10/1985 | Filley et al. | 424/717 |
| 4,886,789 | 12/1989 | Milner | 514/54 |

Primary Examiner—Nathan M. Nutter
Attorney, Agent, or Firm—Venable, Baetjer, Howard & Civiletti

[57] ABSTRACT

Disclosed is a novel therapy involving infusion of specially adapted electrolyte solution comprising essentially physiological concentrations of sodium and other cations and in general higher than physiological concentrations of bicarbonate. The therapy is related to treatment of altered renal function and prophylactic treatment of a patient to resist onset of altered renal function.

8 Claims, No Drawings

INTRAVENOUS SOLUTIONS FOR INFLUENCING RENAL FUNCTION AND FOR MAINTENANCE THERAPY

BACKGROUND OF THE INVENTION

This invention relates to novel intravenous solutions for influencing renal function and for follow-up maintenance therapy. An intravenous solution of the invention is more particularly for treating altered renal function or for prophylactically conditioning the kidney to resist that the kidney enters a condition of altered renal function. The term altered renal function as employed herein means a qualitatively and quantitatively depleted or insufficient production of urine, insufficient clearance of metabolic and toxic substances normally cleared by the kidney such as electrolytes, urea, creatinine, phosphates, endogenous and exogenous toxins, pharmaceuticals and their metabolites, a depleted or insufficient ability of the kidney to acidify the urine by excretion of non-volatile or strong acids, or a depleted or insufficient capability of the kidney to produce bicarbonate and thus inability of the kidney to maintain a metabolic acid-base balance within acceptable limits. In such conditions, the therapy normally involves administration of diuretics, preferably loop diuretics, to encourage diuresis.

The intravenous solution of the invention in general finds application in treating patients preliminary to, during and after surgical intervention or any other condition or treatment which may lead to altered renal function. Examples of treatment with potentially nephrotoxic substances include contrast media, antibiotics, cytostatics, cytotoxic drugs, and immuno suppressive drugs. A wide variety of solutions, some being described as substitution fluids are employed for intravenous administration. Commonly used solutions and their compositions are shown in the following Table I:

TABLE I

| Solution | Solute | Concentrations g/100 ml | ($Na^+$) | ($K^+$) | ($Ca^{2+}$) | ($Cl^-$) | ($HCO_3^-$) |
|---|---|---|---|---|---|---|---|
| Dextrose in water | | | | | | | |
| 5.00% | Glucose | 5.00 | — | — | — | — | — |
| 10.00% | Glucose | 10.00 | — | — | — | — | — |
| Saline | | | | | | | |
| Hypotonoc (0.45%, half normal) | NaCl | 0.45 | 77 | — | — | 77 | — |
| Isotonic (0.9%, normal) | NaCl | 0.90 | 154 | — | — | 154 | — |
| Hypertonic | NaCl | 3.00 | 513 | — | — | 513 | — |
| | | 5.00 | 855 | — | — | 855 | — |
| Dextrose in saline | | | | | | | |
| 5% in 0.22% | Glucose | 5.00 | — | — | — | — | — |
| | NaCl | 0.22 | 38.5 | — | — | 38.5 | — |
| 5% in 0.45% | Glucose | 5.00 | — | — | — | — | — |
| | NaCl | 0.45 | 77 | — | — | 77 | — |
| 5% in 0.9% | Glucose | 5.00 | — | — | — | — | — |
| | NaCl | 0.90 | 154 | — | — | 154 | — |
| Ringer's | NaCl | 0.86 | | | | | |
| | KCl | 0.03 | 147 | 4 | 5 | 156 | — |
| | $CaCl_2$ | 0.03 | | | | | |
| Lactated Ringer's | NaCl | 0.60 | | | | | |
| | KCl | 0.03 | | | | | |
| | $CaCl_2$ | 0.02 | 130 | 4 | 3 | 109 | 28 |
| | Na lactate | 0.31 | | 0.31 | | | |
| Hypertonic sodium bicarbonate (0.6 M) | $NaHCO_3$ | 5.00 | 595 | — | — | — | 595 |
| Hypertonic sodium bicarbonate (0.6 M) | $NaHCO_3$ | 7.50 | 893 | — | — | — | 893 |
| Potassium chloride | KCl | 14.85 | — | 211 | — | 2 | |

Administration of the Dextrose solutions is physiologically equivalent to the administration of distilled water since glucose is rapidly metabolized to $CO_2$ and $H_2O$. The Dextrose is however essential to render the solution isotonic and thus avoid hemolysis. The Saline solutions are most commonly administered since most patients in need of treatment are not only water-depleted but also $Na^+$ depleted, i.e. salt-depleted.

The plasma $Na^+$ concentration can be employed to assist in determining which of the above Dextrose, Saline or Dextrose in Saline solutions is most appropriate. The Dextrose solutions provide a small amount of calories, for example the 5% Dextrose or 5% Dextrose in 0,22% saline is equivalent to 200 kcal per liter of solution.

The Ringer's solutions comprised in the above Table include physiologic amounts of $K^+$ and $Ca^{++}$ in addition to NaCl. The lactated Ringer's solution comprising 28 mEq of lactate per liter (which metabolizes to $HCO_3^-$) has a composition close to that of extracellular fluid.

The hypertonic Sodium bicarbonate solutions are primarily employed in the treatment of metabolic acidosis for example by administration of a 7.5% or higher solution comprised in 50 ml ampuls, but can be added to other intravenous solutions, however not including the Ringer's solutions since precipitation of the $HCO_3^-$ with the $Ca^{++}$ would take place. Similarly, the Potassium Chloride solution can be added to other intravenous solutions, but care needs to be taken not to intravenously administer any concentrated solution of $K^+$ since this can produce an excessive or too rapid increase in plasma concentration of $K^+$, which can be fatal.

Other than the above-mentioned hypertonic Sodium bicarbonate solutions, none of the above solutions are known to have any specific influence on kidney function. The hypertonic Sodium bicarbonate solutions on the other hand are normally administered only in limited quantities, at most in quantities sufficient to temporarily correct, normally only in part, a condition of metabolic acidosis. Suggestions to intravenously administer higher quantities of the available Sodium bicarbonate solutions has met with understandable resistance in view particularly of the fact that such solutions are strongly hypertonic and all comprise very much more than or less than physiological amounts of cation solute. Thus, for example the above-mentioned higher concentration 7.5% Sodium bicarbonate solution available in 50 ml ampuls comprises about 900 mval of $Na^+$, and 900 mval of $HCO_3^-$ per liter of solution which is neither physiological for $Na^+$ nor for $HCO_3^-$. In contrast, the normal value for $Na^+$ in the blood is from 135 to 146 mval/liter and the normal value for $HCO_3^-$ is 22 to 26 mval/liter.

SUMMARY OF THE INVENTION

In accordance with the invention, it has been found that relatively large quantities of a solution comprising higher than physiological concentrations of $HCO_3^-$ can be intravenously administered provided that the Sodium content of the solution is not significantly different from physiological levels, i.e. not significantly different from about 135 to about 146 mval/liter. Sodium is the most important electrolyte cation and any significant deviation from physiological concentrations as could arise from i.v. administration of any larger quantity of intravenous solution containing more or less than physiological levels of $Na^+$ may create undesirable and dangerous side effects. Thus, if for example any substantial quantity, say in excess of 200 ml, of the 7.5% (0.9M) i.v. sodium bicarbonate solution discussed above were administered to a patient, the patient would tend towards a condition of hypersodemia which has toxic consequences. A condition of hyposodemia similarly can have life endangering consequences so that in general and presuming that the sodium levels in the serum of the patient are within physiological limits, the intravenous solution of the invention comprises a sodium concentration which substantially matches physiological concentrations. On the other hand, as already indicated, the bicarbonate anion concentration in the solution can be very substantially higher than physiological concentrations. However, concentrations of bicarbonate as high as those comprised in known sodium bicarbonate intravenous solutions are not contemplated. The reason is that an excessive or too rapid an increase of bicarbonate in plasma can be fatal as a consequence of systemic alkalosis or hypercapnea (excessive $CO_2$ concentration arising from decomposition of $HCO_3^-$ into $CO_2$ and $H_2O$). Other anions and cations comprised in the intravenous solution of the invention would in general be within or close to physiological levels. Thus, potassium cation would normally be present in the solution at physiological concentrations but could be left away especially if the patient is inclined to hyperkalemia as is sometimes the case. Similarly, chloride anion would be present at physiological levels but can be lower, which latter solution can find use for a patient which is in a condition of hyperchloremic acidosis, as is also sometimes the case.

In the major proportion of cases in which intravenous infusion of fluids is required, the functioning of the kidney of the patient, even if the kidney was initially healthy, may have been or will be altered by a planned medical intervention. For example, renal dysfunction and failure can be a result of heavy injury or massive intervention. Also, however, many patients requiring infusion of fluids, are in any case already suffering from altered or impaired renal function, e.g. because of age or pre-existing disease. Kidney functions are inadequate in a large majority of cases and it is an object of the present invention to provide a novel intravenous solution which is able in particular to acidify the urine, i.e. to increase the capacity of the kidney to excrete hydrogen ions and metabolic acids in the urine, and to increase the volume of urine i.e. the excretion of excess water, (along with increased clearance of substances normally entrained in the urine). Furthermore, in general, the novel solutions of the present invention can serve to correct any systemic acid-base or electrolyte disorders which may be associated with a condition of acute or chronic renal failure or prevention thereof requiring treatment by intravenous infusion of fluids.

The intravenous solutions of the invention essentially act on the whole length of the renal nephron-segments, i.e. the renal tubulae, in particular on the proximal tubulae, whereas loop diuretics essentially act on the distal tubulae. A combination of the two effects enables the action of the loop diuretic to be potentiated which can offer means for reducing the dose required, and diuresis to be increased. The supply of bicarbonate contained in the solutions of the invention provide an essential substrate for beneficial conditioning renal function.

DETAILED DESCRIPTION OF THE INVENTION

An intravenous solution in accordance with the invention comprises at least the following anions and cations, in amounts, i.e. concentrations, within the ranges indicated in the following Table II:

|  | mval/liter | (preferably) |
|---|---|---|
| $Na^+$ | 130 to 150 | 135 to 146 |
| $K^+$ | 0 to 6 | 2 to 5 |
| $Cl^-$ | 80 to 125 | 90 to 110 |
| $HCO_3^-$ | 25 to 30 to 70 | 40 to 60 |

A typical solution useful for treating altered renal function comprises the following amounts and concentrations of electrolytes:

|  |  |  | mval/liter |
|---|---|---|---|
| Sodium Chloride | 5.026 g | $Na^+$ | 146 |
| Potassium Chloride | 0.298 g | $K^+$ | 4 |
| Sodium Bicarbonate | 5.040 g | $Cl^-$ | 90 |
| Water for infusion solution to | 1000.0 ml | $HCO_3^-$ | 60 |

Once treatment with a solution such as above has achieved the desired results for a reasonable period, i.e. increased urine volume and stabilized acid-base balance for 24 hours or more, a solution comprising less bicarbonate ions, i.e. less than 40 mval/liter but not lower than physiological levels, i.e. 25 mval/liter may be employed for maintenance therapy. However, since it is important that sodium levels not depart significantly from physiological levels, lowering of the bicarbonate content requires an increase in Sodium Chloride content which in turn leads to an increase in Chloride content. Hyperchloremia is often attendant to altered renal function so that increased chloride above physiological levels would in general be avoided.

The dose of intravenous solution administered will of course depend on the weight of the patient, the condition of the patient, specifically the fluid balance, and the effect desired. However, in general, satisfactory results for treating altered renal function and achievement of increased urine volume and associated desired results such as increased clearance of metabolites and toxins, fixed or strong acids, phosphates and the like are obtained when a solution comprising more than about 40 mval/liter of bicarbonate anion is administered at a rate of from 50 to 500 ml of solution/hour (about 15 to 180 drops/min). The total dose required for an adult in twenty-four hours can be as much as 12 liters (=500 ml/hour). An indication of whether or not the dose is adequate can be obtained by blood gas analysis and by measuring fresh urine pH value. If the urine pH value tends towards or is slightly greater than 7.0, adequate dosage has been achieved. Exemplary clinical trials performed with a bicarbonate-electrolyte solution of the invention are summarized below. The six patients were all urological post-operative patients suffering from prostate or kidney carcinoma.

Diagnosis: Prostate-Carcinoma
Operation: Radical Lymphadenectomy
Progression: Diuresis:
  1st day: 1085 ml
  2nd day: 4130 ml
  3rd day: 5270 ml
  4th day: 4600 ml
  5th day: 1550 ml up to 6 p.m.
  (otherwise from 6 a.m. to 6 a.m.)
Infusion program:
1st day:
  3000 ml Bicarbonate-electrolyte solution
  1000 ml Glucose 5%
2nd day:
  2000 ml Combiplasmal
  2000 ml Bicarbonate-electrolyte solution +20 mg Lasix +40 mval KCl
  1000 ml Ringer
3rd day:
  2000 ml Bicarbonate-electrolyte solution +20 mg Lasix +40 mval KCl
  2000 ml Combiplasmal
  500 ml Glucose 5%
  1000 ml Ringer
4th day:
  2000 ml Bicarbonate-electrolyte solution +20 mg Lasix +40 mval KCl
  1000 ml Glucose 5%
  160 ml Combiplasmal
  1000 ml Aminosteril 10%
  2000 ml Ringer
5th day:
  500 ml Aminosteril 10%
  500 ml Glucose 5%
  1000 ml Ringer
  1000 ml Bicarbonate-electrolyte solution +20 mg Lasix +20 mval KCl infused up to 6 p.m.
Balance:
  1st day: 2715 ml
  2nd day: 870 ml
  3rd day: 680 ml
  4th day: 1310 ml
  5th day: no balance established
Serum values:
1st day:
  pH 7,37, $PCO_2$ 39 mmHg, $HCO_3^-$ 23 mmol/l, BA $-1.6$.
2nd day:
  pH 7,42, $PCO_2$ 42 mmHg, $HCO_3^-$ 28 mmol/l, BA $+3.6$.
  Urea-N. 27 mg/dl (7-18), Creatinine 2,3 mg/dl, Ca 8,4 mg/dl.
  Phosphorous (inorg) 5,5 mg/dl, Protein 5,2 g/dl (other values normal).
3rd day:
  all values normal except Urea-N. 26 mg/dl, Creatinine 2,0 mg/dl.
  Uric acid 8,3 mg/dl, $K^+$ 3,2 mmol/l.
4th day:
  all values normal except Urea-N. 25 mg/dl, Creatinine 1,6 mg/dl.
  $K^+$ 3,3 mmol/l, Protein 5,6 g/dl.
5th day:
  pH 7,41, $PCO_2$ 46 mmHg, $HCO_3^-$ 29 mmol/l, BA $+4,2$.
  Urea-N. 33 mg/dl, Creatinine 1,5 mg/dl, $K^+$ 3,4 mmol/l, Ca 8,5 mg/dl, Protein 5,9 g/dl.
Normal range of Serum values:
Blood gas analysis, venous blood:
  pH: 7,32-7,38
  $PCO_2$: 42-50 mmHg
  $HCO_3^-$: 23-27 mmol/l
  BA: $0\pm2,3$ mmol/l (BA=base excess/or deficit value)
Serum values:
  Urea-N: 7-18 mg/dl
  Creatinine: 0,5-1,3 mg/dl
  Uric acid: 3-7 mg/dl
  Phosphorous (inorg): 2,5-4,5 mg/dl
  Protein: 6,0-8,0 g/dl
  $Na^+$: 135-146 mmol/l
  $K^+$: 3,5-5,0 mmol/l
  $Cl^-$: 97-108 mmol/l
  Calcium (total): 8,7-10,5 mg/dl Summary High daily urine volumes, uncomplicated progression. Transferred to General clinic on 5th postoperative day. Adequate control of serum metabolites concentration. Electrolyte and acid-basis-balance essentially normal, mild potassium- and Protein-deficit. Observation period 5 days.

Diagnosis: Kidney-Carcinoma
Operation: Nephrectomy
Progression: Diuresis:
  1st day: 2280 ml
  2nd day: 2020 ml
  3rd day: 1700 ml (intensive transpiration)
  4th day: 2640 ml
Infusion program:
1st day:
  2000 ml Bicarbonate-electrolyte solution +20 mg Lasix +40 mval KCl
  1000 ml Glucose 5%
2nd day:
  1000 ml Glucose 5%
  2000 ml Bicarbonate-electrolyte solution +40 mval KCl +20 mg Lasix
3rd day:
  2000 ml Bicarbonate-electrolyte solution +40 mval KCl +20 mg Lasix
  1000 ml Glucose 5%

500 ml Ringer
4th day:
  2000 ml Bicarbonate-electrolyte solution +20 mg Lasix +40 mval KCl
  1000 ml Glucose 5%
5th day:
  2000 ml Bicarbonate-electrolyte solution +20 mg Lasix +40 mval KCl
  1000 ml Glucose 5%
6th day:
  1000 ml Bicarbonate-electrolyte solution
  500 ml Glucose 5%
Balance:
  1st day: +570 ml
  2nd day: +1530 ml
  3rd day: +1600 ml
  4th day: +1000 ml
  5th day: +1300 ml
Serum values:
1st day:
  not determinated.
2nd day:
  Uriea-N 19 mg/dl, Creatinine 1,8 mg/dl, Ca 7,8 mg/dl, Protein 5,4 g/dl, (other values normal).
  pH 7,45, $PCO_2$ 45 mmHg, $HCO_3^-$ 31 mmol/l, BA +7,1.
3rd day:
  Urea-N 34 mg/dl, Creatinine 2,5 mg/dl, Uric-acid 7,6 mg/dl.
  Ca 8,1 mg/dl, Protein 5,6 g/dl, (other values normal).
  pH 7,49, $PCO_2$ 40 mmHg, $HCO_3^-$ 30 mmol/l, BA +7,1.
4th day:
  Urea-N 49 mg/dl, Creatinine 2,4 mg/dl, Ca 7,4 mg/dl, Protein 5,2 g/dl, (other values normal).
5th day:
  pH 7,46, $PCO_2$ 33 mmHg, $HCO_3^-$ 23 mmol/l, BA +1,1.
  Urea-N 46 mg/dl, Creatinine 2,0 mg/dl, Protein 5,6 g/dl, Ca 8,0 mg/dl, (other values normal).
6 th day:
  Urea-N 37 mg/dl, Creatinine 1,9 mg/dl, Ca 8,2 mg/dl.

Summary

High daily urine volumes. The observation period ended on the 6th day, when the patient was transferred to the General clinic. In general satisfactory progress. Essentially stabilized acid/base status, including serum concentration of metabolites, electrolytes, Na, K, Cl always at normal levels.
Diagnosis: Prostata-Carcinoma
Operation: Radical Prostatectomy, Pelvine Lymphadenectomy
Progression: Diuresis:
  1st day: 1380 ml
  2nd day: 4400 ml
  3rd day: 4100 ml
  4th day: 4250 ml
  5th day: 4450 ml
  6th day: 4100 ml
Infusion program:
1st day (after 3 p.m.):
  1000 ml Bicarbonate-electrolyte solution
  1000 ml Glucose 5%
  1000 ml Ringer
2nd day:
  2000 ml Combiplasmal
  500 ml Lipofundin
  500 ml Glucose 5%
  2000 ml Bicarbonate-electrolyte solution +20 mg Lasix +40 mval KCl
  500 ml Glucose 5%
3rd day:
  2000 ml Bicarbonate-electrolyte solution
  2000 ml Combiplasmal
  1000 ml Glucose 5%
  500 ml Lipofundin
4th day:
  500 ml Lipofundin
  2000 ml Combiplasmal +20 mval KCl
  2000 ml Bicarbonate-electrolyte solution +20 mg Lasix +40 mval KCl
  100 ml Humanalbumin
5th day:
  500 ml Lipofundin
  2000 ml Bicarbonate-electrolyte solution +20 mg Lasix +40 mval KCl
  2000 ml Combiplasmal +20 mval KCl
  500 ml Glucose 5%
  1000 ml Ringer
6th day:
  500 ml Lipofundin
  1000 ml Combiplasmal
  2000 ml Bicarbonate-electrolyte solution +20 mg Lasix +40 mval KCl
  500 ml Glucose 5%
7th day:
  500 ml Lipofundin
  500 ml Glucose 5%
  1000 ml Combiplasmal
  1000 ml Bicarbonate-electrolyte solution +20 mg Lasix +20 mval KCl
  all drugs until 12 a.m. then transferred
Balance:
  1st day: +1670 ml
  2nd day: +350 ml
  3rd day: +1550 ml
  4th day: +1120 ml
  5th day: +2280 ml
  6th day: +750 ml
Serum values:
1st day:
  pH 7,36, $PCO_2$ 48 mmHg, $HCO_3^-$ 27 mmol/l, BA +1,5.
2nd day:
  Protein 4,9 g/dl (6-8), Ca 7,6 mg/dl (8,7-10,5), other values normal.
  pH 7,41, $PCO_2$ 39 mmHg, $HCO_3^-$ 25 mmol/l, BA +1,3.
3rd day:
  Potassium 3,4 mmol/l, Protein 4,9 g/dl (6-8), pH 7,41, $PCO_2$ 48 mmHg, $HCO_3^-$ 31 mmol/l, BA +5,6.
4th day:
  Potassium 3,3 mmol/l, Ca 7,8 mg/dl, Protein 4,7 g/dl, pH 7,43, $PCO_2$ 39 mmHg, $HCO_3^-$ 27 mmol/l, BA +3,1.
5th day:
  Potassium 3,5 mmol/l, Ca 8,2 mg/dl, Protein 5,3 g/dl, pH 7,42, $PCO_2$ 42 mmHg, $HCO_3^-$ 27 mmol/l, BA +2,5.
6th day:
  Ca 8,0 mg/dl (8,7-10,5), Protein 5,1 g/dl, pH 7,42, $PCO_2$ 42 mmHg, $HCO_3^-$ 27 mmol/l, BA +2,6.
7th day:

Ca 8,1 mg/dl, Protein 5,1 g/dl, pH 7,42, PCO$_2$ 41 mmHg, HCO$_3^-$ 27 mmol/l, BA +2,6.

Summary

Very high daily urine volumes. Uncomplicated progression, stabilized metabolites, electrolytes and acid-basis-balance, mild potassium-, calcium- and protein-deficit. Transferred to General clinic on 7th postoperative day.
Diagnosis: Kidney-Carcinoma
Operation: Nephrectomy
Progression: Diuresis:
  1st day: 2760 ml
  2nd day: 620 ml up to 10 a.m.
Infusion program:
1st day:
  1000 ml Bicarbonate-electrolyte solution
  2000 ml Bicarbonate-electrolyte solution +20 mg Lasix +40 mval KCl
  500 ml Glucose 5%
  500 ml Ringer
2nd day:
  1000 ml Combiplasmal
  1000 ml Bicarbonate-electrolyte solution +20 mval KCl +10 mg Lasix
  250 ml Glucose 50%, up to 10 a.m.
Balance:
  1st day: +1240 ml
  2nd day: not evaluated
Serium values:
1st day:
  normal.
2nd day:
  Protein 4,9 g/dl, Creatinine mg/dl 1,4 mg/dl, Calcium 7,8 mg/dl, pH 7,44, PCO$_2$ 45 mmHg, HCO$_3^-$ 30 mmol/l, BA +6.

Summary

High daily urine volumes. Uncomplicated progression. Transferred to General clinic on 2nd postoperative day. Stabilized metabolites electrolytes and acid-basis balance. Mild protein- and Ca-deficit.
Diagnosis: Kidney-Carcinoma
Operation: Ventral Nephrectomy with Lymphadenectom
Progression: Diuresis:
  1st day: 2800 ml
  2nd day: 2700 ml
Infusion program:
1st day:
  1000 ml Ringer (OP)
  2000 ml Bicarbonate-electrolyte solution +20 mg Lasix +40 mval KCl
2nd day:
  2000 ml Combiplasmal
  2000 ml Bicarbonate-electrolyte solution +20 mg Lasix +40 mval KCl
  500 ml Glucose 5%
Balance:
  1st day: +200 ml
  2nd day: +1700 ml
Serum values:
1st day:
  not evaluated.
2nd day:
  normal except Creatinine mg/dl 2,0 mg/dl.
  pH 7,43, PCO$_2$ 42 mmHg, HCO$_3^-$ 28 mmol/l, BA +3,9.

Summary

High daily urine volumes. Progression without complications. Observation period 2 days. Metabolites concentration, electrolytes and blood gases essentially normal.
Diagnosis: Stenosis of Urethra, Prostata-Carcinoma, Diab. mellitus
Operation: Pelvine Lymphadenectomy
Progression: Diuresis:
  1st day: 2880 ml
  2nd day: 2200 ml
  3rd day: 4030 ml
Infusion program:
1st day:
  2000 ml Bicarbonate-electrolyte solution, +20 mg Lasix +40 mval KCl
  1000 ml Glucose 5%
2nd day:
  2000 ml Bicarbonate-electrolyte solution, 40 mval KCl, 20 mg Lasix
  1000 ml Glucose 5%
3rd day:
  2000 ml Bicarbonate-electrolyte solution, +40 mval KCl, 20 mg Lasix
4th day:
  1000 ml Bicarbonate-electrolyte solution, +40 mval KCl, 20 mg Lasix
Balance:
  1st day: −470 ml
  2nd day: +1490 ml
  3rd day: −530 ml
Serum values:
1st day:
  Urea-N. 21 mg/dl (norm 7–18), Uric acid 8,9 mg/dl (−7).
  other values normal.
2nd day:
  mild higher value of Urea N. and Uric acid.
  Protein 4,9 g/dl (6–8), Ca 7,8 mg/dl (8,7–10,5).
  pH 7,41, PCO$_2$ 49 mmHg, HCO$_3^-$ 31 mmol/l, BA +5,4.
3rd day:
  Chloride 96 mmol/l (97–108), Ca. 7,8 mg/dl, Protein 4,9 g/dl.
  other values normal.
  pH 7,49, PCO$_2$ 48 mmHg, HCO$_3^-$ 37, BA +12,5
4th day:
  Uric acid. 8,9 mg/dl, Potassium 3,4 mmol/l, Ca 8 mg/dl.
  Phosphor 2,3 mg/dl (2,5–4,5), Protein 4,9 g/dl.
  other values normal

Summary

High daily urine volumes. Stabilized metabolites, electrolytes-values, Protein mildly lower. Transferred to General clinic on 4th postoperative day=end of observation. Uncomplicated progression.

Of course, the solutions of the invention may comprise additional substances, such as pharmaceuticals, trace elements soluble and stable Ca and/or Mg compounds.

What is claimed is:

1. A method of treating a human patient suffering from altered renal function or prophylactically conditioning the human patient so that the kidneys resist entering a condition of altered renal function, which comprises the step of intravenously administering to a patient in need thereof a therapeutically effective amount of a sterile solution comprising at least the following electrolytes at the concentrations indicated:

|  | mval/liter |
| --- | --- |
| $Na^+$ | 130 to 150 |
| $K^+$ | 0 to 6 |
| $Cl^-$ | 80 to 125 |
| $HCO_3^-$ | 25 to 70 |

2. A method according to claim 1, in which the sterile solution comprises the electrolytes at the following concentrations:

|  | mval/liter |
| --- | --- |
| $Na^+$ | 135 to 146 |
| $K^+$ | 2 to 5 |
| $Cl^-$ | 90 to 110 |
| $HCO_3^-$ | 40 to 60 |

3. A method according to claim 1, in which the therapeutically effective amount is within the range of 50 to 500 ml/hour.

4. A method according to claim 1, in which the treatment is accompanied by administration of a therapeutically effective amount of a loop diuretic.

5. A method according to claim 1, in which the treatment is followed by maintenance therapy involving administration of a sterile solution comprising at least the following electrolytes at the concentrations indicated:

|  | mval/liter |
| --- | --- |
| $Na^+$ | 130 to 150 |
| $K^-$ | 0 to 6 |
| $Cl^-$ | 80 to 125 |
| $HCO_3^-$ | 25 to 30 |

6. A sterile intravenous solution comprising at least the following electrolytes at the concentrations indicated:

|  | mval/liter |
| --- | --- |
| $Na^+$ | 130 to 150 |
| $K^+$ | 2 to 5 |
| $Cl^-$ | 80 to 125 |
| $HCO_3^-$ | 25 to 70 |

7. A sterile intravenous solution according to claim 6, comprising the electrolytes at the following concentrations:

|  | mval/liter |
| --- | --- |
| $Na^+$ | 135 to 146 |
| $K^+$ | 2 to 5 |
| $Cl^-$ | 90 to 110 |
| $HCO_3^-$ | 40 to 60 |

8. A sterile intravenous solution according to claim 6, comprising the electrolytes at the following concentration:

|  | mval/liter |
| --- | --- |
| $Na^+$ | 135 to 146 |
| $K^-$ | 2 to 5 |
| $Cl^-$ | 90 to 110 |
| $HCO_3^-$ | 25 to 30 |

* * * * *